US010188625B2

(12) United States Patent
Castex-Rizzi et al.

(10) Patent No.: US 10,188,625 B2
(45) Date of Patent: Jan. 29, 2019

(54) COMBINATION OF A RETINOID AND A DIOL AND POLYUNSATURATED FATTY ACID ESTER

(71) Applicant: PIERRE FABRE DERMO-COSMETIQUE, Boulogne-billancourt (FR)

(72) Inventors: Nathalie Castex-Rizzi, Colomiers (FR); Daniel Redoules, Toulouse (FR); Sandrine Bessou-Touya, Caujac (FR); Jean-Hilaire Saurat, Geneva (CH)

(73) Assignee: PIERRE FABRE DERMO-COSMETIQUE, Boulogne Billancourt (FR)

( * ) Notice: Subject to any disclaimer, the term of this patent is extended or adjusted under 35 U.S.C. 154(b) by 0 days.

(21) Appl. No.: 15/553,882

(22) PCT Filed: Feb. 29, 2016

(86) PCT No.: PCT/EP2016/054227
§ 371 (c)(1),
(2) Date: Aug. 25, 2017

(87) PCT Pub. No.: WO2016/135340
PCT Pub. Date: Sep. 1, 2016

(65) Prior Publication Data
US 2018/0036275 A1    Feb. 8, 2018

(30) Foreign Application Priority Data

Feb. 27, 2015 (FR) ..................... 15 51714

(51) Int. Cl.
*A61K 31/232* (2006.01)
*A61K 8/67* (2006.01)
*A61Q 19/00* (2006.01)
*A61K 8/37* (2006.01)
*A61K 31/07* (2006.01)

(52) U.S. Cl.
CPC ............ *A61K 31/232* (2013.01); *A61K 8/375* (2013.01); *A61K 8/671* (2013.01); *A61K 31/07* (2013.01); *A61Q 19/008* (2013.01); *A61K 2300/00* (2013.01)

(58) Field of Classification Search
None
See application file for complete search history.

(56) References Cited

U.S. PATENT DOCUMENTS 8,623,916 B2 * 1/2014 Redoules .............. C07C 69/587
514/549
2011/0230557 A1    9/2011 Redoules et al.

FOREIGN PATENT DOCUMENTS

EP        0807429 A1    11/1997
WO    WO 2010/072738 A1    7/2010

OTHER PUBLICATIONS

Cunliffe et al., "Comedone formation: etiology, clinical presentation, and treatment," Clinics in Dermatology, vol. 22, 2004, pp. 367-374.
Everts, "Endogenous retinoids in the hair follicle and sebaceous gland," Biochimica et Biophysica Acta, vol. 1821, No. 1, Jan. 2012, pp. 222-229 (pp. 1-18).
Fort-Lacoste et al., "Comedolytic effect of topical retinaldehyde in the rhino mouse model," Dermatology, vol. 199, Suppl. 1, 1999, pp. 33-35.
Lucky et al., "A multirater validation study to assess the reliability of acne lesion counting," Journal of the American Academy of Dermatology, vol. 35, No. 4, Oct. 1996, pp. 559-565.
Maeda, "An Electron Microscopic Study of Experimentally-induced Comedo and Effects of Vitamin A Acid on Comedo Formation," The Journal of Dermatology, vol. 18, 1991, pp. 397-407.
Poli et al., "Efficacy and Safety of 0.1% Retinaldehyde/ 6% Glycolic Acid (Diacnéal®) for Mild to Moderate Acne vulgaris," Dermatology, vol. 210, Suppl. 1, 2005, pp. 14-21.
Shaheen et al., "Acne sans P. acnes," Journal of the European Academy of Dermatology and Venereology, vol. 27, 2013, pp. 1-10.
Thielitz et al., "Topical retinoids in acne—an evidence-based overview," JDDG, vol. 8, Suppl. 1, 2010, pp. S15-S23, with an English abstract. Reproduced from JDDG, vol. 6, 2008, pp. 1023-1031.

* cited by examiner

Primary Examiner — Brian J Davis
(74) Attorney, Agent, or Firm — Birch, Stewart, Kolasch & Birch, LLP

(57) ABSTRACT

The present invention concerns a combination of a retinoid and a diol and polyunsaturated fatty acid ester, a dermatological or dermocosmetic composition containing such a combination and use of same in the treatment of acne and the prevention of retentional lesions. The present invention also concerns a retinoid, optionally in combination with a diol and polyunsaturated fatty acid ester, for use in the prevention of retentional lesions.

21 Claims, 1 Drawing Sheet

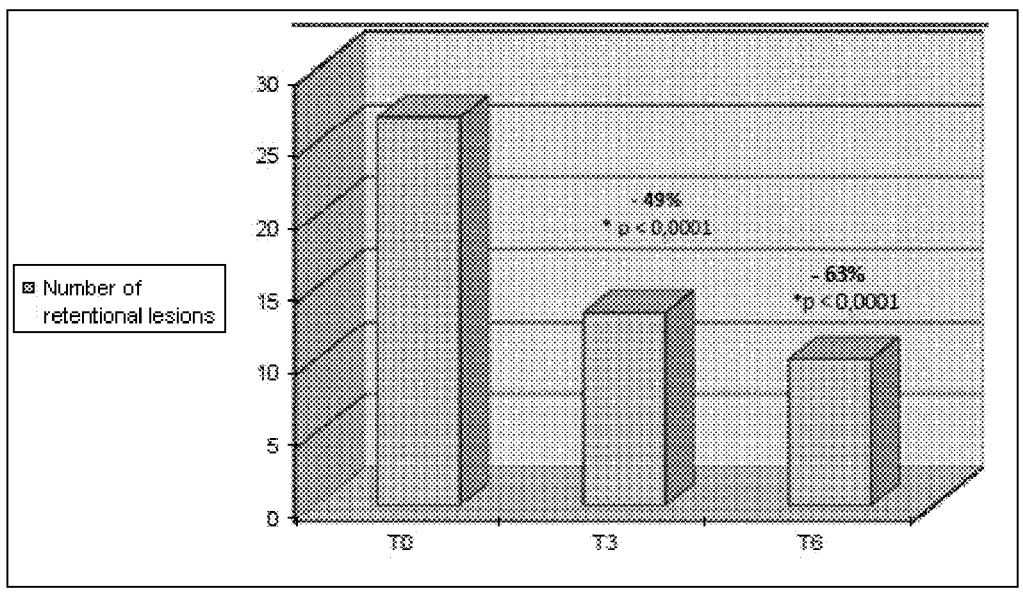

COMBINATION OF A RETINOID AND A DIOL AND POLYUNSATURATED FATTY ACID ESTER

The field of the present invention concerns a combination of a retinoid and a diol and polyunsaturated fatty acid (PUFA) ester, as well as a topical dermatological or dermocosmetic composition containing such a combination, in particular for preventing the formation of retentional acne lesions.

Among retentional acne lesions, open comedones (blackheads) are distinguished from closed comedones, also called microcysts or whiteheads (raised white elements, 1 to 3 mm in diameter).

It is in the presence of comedogenic factors that the differentiation program of infundibular canal cells is modified. This process induces progressive keratinization, and thus thickening, of the pilosebaceous duct (hyperkeratosis), which leads to formation of the comedo, i.e., a retentional lesion, due to the obstruction of said duct.

Thus, a novel approach to the care of acne-prone skin is to target an active agent, for topical application, capable of preventing the appearance of new retentional lesions by preventing the switching of the healthy pilosebaceous unit in the acne cycle.

The leading factors capable of inducing this switching and allowing the formation of the comedo include the bacterium *P. acnes*, which acts by various mechanisms (Shaheen B and Gonzalez M (2013)), comedogenic environmental factors, and vitamin A deficiency in the pilosebaceous epithelium (Everts HB (2012)). Correcting or protecting against these factors can prevent normal sebaceous follicles from entering the acne cycle.

In this context, the Applicant has surprisingly shown that a retinoid such as retinaldehyde, alone or in combination with a diol and polyunsaturated fatty acid (PUFA) ester, prevented the formation of retentional lesions. More particularly, the results of the studies showed the role of retinaldehyde (also called retinal) in protecting the infundibular canal by its prophylactic effect on thickening/keratinization of the canal. Moreover, retinaldehyde prevents vitamin A deficiency in acne-prone skin. Thus retinoids, and more particularly retinaldehyde, can now be used to prevent the formation of retentional lesions.

The first object of the present invention is thus a combination of a retinoid and a diol and polyunsaturated fatty acid ester as disclosed in WO 2010/072738.

The present invention thus relates to a combination comprising a retinoid and a compound of the following general formula (I):

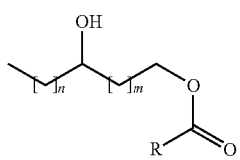

wherein:
n is an integer between 0 and 15, in particular between 1 and 15,
m is 0, 1, 2 or 3, and
R is the hydrocarbon chain of a polyunsaturated fatty acid selected from omega-3s and omega-6s.

The retinoid used in the context of this combination can be selected from retinol, retinaldehyde, and retinoic acid in its various isomeric forms (in particular all-trans, 13-cis and 9-cis). It can be in particular retinol or retinaldehyde. Preferably the retinoid is retinaldehyde.

By "isomeric forms" of a compound are meant, in the context of the present invention, the various stereoisomers of said compound, i.e. the geometric isomers and optical isomers.

The geometric isomers, also called E/Z isomers or cis-trans isomers, result from the different position of substituents on a double C=C bond which can have a Z or E configuration, also called cis or trans configuration.

The optical isomers result from the different position in space of substituents or lone pair of electrons on an atom (such as a carbon or sulphur atom) comprising four different substituents (including potentially a lone pair of electron). This atom thus represents a chiral or asymmetric center. Optical isomers which are not mirror images of one another are thus designated as "diastereoisomers," and optical isomers which are non-superimposable mirror images are designated as "enantiomers".

By "polyunsaturated fatty acid" is meant, in the context of the present invention, a linear carboxylic acid ($R1CO_2H$) comprising 10 to 28, preferably 16 to 24, and more preferably 18 to 22, carbon atoms (including the carbon atom of the carboxylic acid function) and comprising at least 2, preferably 2 to 6, C=C double bonds, said double bonds preferably having a cis configuration.

By "hydrocarbon chain of a polyunsaturated fatty acid" is meant, in the context of the present invention, the hydrocarbon chain (R1) linked to the acid function of the polyunsaturated fatty acid ($R1CO_2H$). R1 is thus a linear hydrocarbon chain comprising 9 to 27, preferably 15 to 23, and more preferably 17 to 21, carbon atoms and comprising at least 2, preferably 2 to 6, C=C double bonds, said double bonds preferably having a cis configuration. Thus, in the case of the linoleic acid of the following formula:

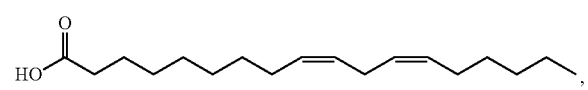

the hydrocarbon chain in question is the following chain:

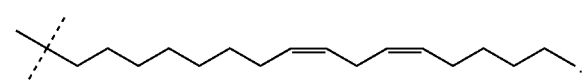

By "omega-3" is meant, in the context of the present invention, a polyunsaturated fatty acid, as defined above, wherein the first double bond of the chain corresponds to the third carbon-carbon bond counting from the end opposite the carboxylic acid function, as illustrated with the α-linolenic acid below:

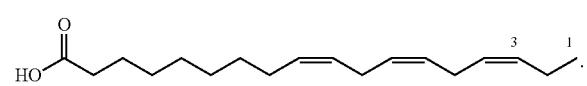 [SMILES: CC/C=C\C/C=C\C/C=C\CCCCCCCC(=O)O]

Omega-3s can in particular be α-linolenic acid, stearidonic acid, eicosatrienoic acid, eicosatetraenoic acid, eicosapentaenoic acid, docosapentaenoic acid, docosahexaenoic acid, tetracosapentaenoic acid and tetracosahexaenoic acid, and preferably it is α-linolenic acid or stearidonic acid, and more particularly α-linolenic acid, which have anti-inflammatory properties.

By "omega-6" is meant, in the context of the present invention, a polyunsaturated fatty acid, as defined above, wherein the first double bond of the chain corresponds to the sixth carbon-carbon bond counting from the end opposite the carboxylic acid function, as illustrated with the linoleic acid below:

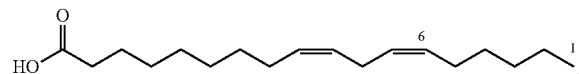

Omega-6s can in particular be linoleic acid, gamma-linolenic acid, eicosadienoic acid, dihomo-gamma-linolenic acid, arachidonic acid, docosatetraenoic acid, docosapentaenoic acid, adrenic acid and calendic acid, and preferably it is linoleic acid, which has sebum-control properties.

In particular, n can be 0, 1, 2, 3, 4 or 5, and preferably 5. Advantageously, n≥3 and preferably n≥5.

Advantageously, m is 0 or 1.

Advantageously, n+m≥3 and preferably n+m≥5.

Advantageously, the hydrocarbon chain R comes from a polyunsaturated fatty acid selected from α-linolenic acid, stearidonic acid, eicosatrienoic acid, eicosatetraenoic acid, eicosapentaenoic acid, docosapentaenoic acid, docosahexaenoic acid, tetracosapentaenoic acid, tetracosahexaenoic acid, linoleic acid, gamma-linolenic acid, eicosadienoic acid, dihomo-gamma-linolenic acid, arachidonic acid, docosatetraenoic acid, docosapentaenoic acid, adrenic acid and calendic acid. Preferably, the polyunsaturated fatty acid will be selected from α-linolenic acid, stearidonic acid and linoleic acid, and more preferably from α-linolenic acid and linoleic acid. Preferably, the fatty acid will be α-linolenic acid.

In particular, the compound of formula (I) can be selected from the following molecules:

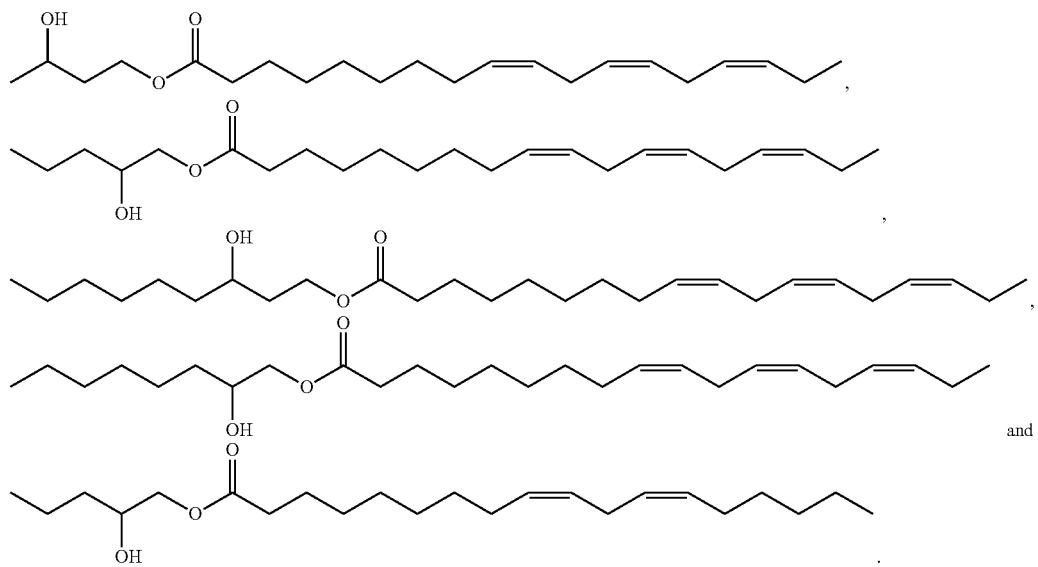

and

Preferably, the compound of formula (I) is the following compound (hereafter "Compound A"):

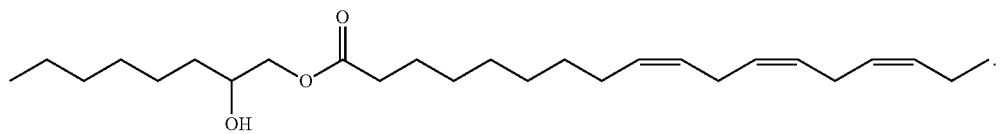 [SMILES: CC/C=C\C/C=C\C/C=C\CCCCCCCC(=O)OCC(O)CCCCCC]

The combination of the invention will preferably be a combination of retinaldehyde as the retinoid with the following Compound A as the compound of formula (I):

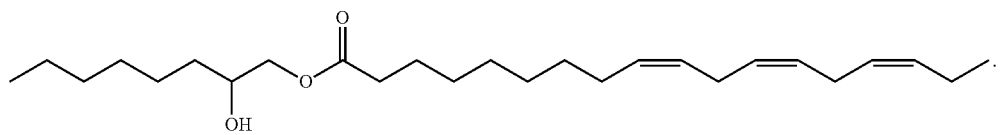 [SMILES: CC/C=C\C/C=C\C/C=C\CCCCCCCC(=O)OCC(O)CCCCCC]

Another object of the present invention is a combination as defined above for use as a medicine, in particular for preventing the formation of retentional lesions.

The present invention also concerns the use of a combination as defined above for the manufacture of a dermatological or dermocosmetic composition, in particular topical, in particular for preventing the formation of retentional lesions.

The present invention also concerns the use of a combination as defined above for preventing the formation of retentional lesions.

The present invention also concerns a method for preventing the formation of retentional lesions comprising the administration of an effective amount of a combination as defined above to a person in need thereof.

The combination according to the present invention is more particularly for preventing the formation of retentional lesions in people with acne-prone skin.

It can reasonably be envisaged to use the combination as defined above in the treatment of acne.

Another object of the present invention is thus the combination as defined above for use in the treatment of acne.

The present invention thus also concerns the use of a combination as defined above for the manufacture of a dermatological or dermocosmetic composition, in particular topical, intended to treat acne.

The present invention also concerns the use of a combination as defined above in the treatment of acne.

The present invention also concerns a method for treating acne comprising the administration of an effective amount of a combination as defined above to a person in need thereof.

Another object of the present invention is a dermatological or dermocosmetic composition comprising at least one combination as defined above in association with at least one dermatologically or dermocosmetically acceptable excipient, more particularly for topical application.

In the present invention, by "dermatologically or dermocosmetically acceptable" is meant that which is useful in the preparation of a dermatological or dermocosmetic composition, which is generally safe, nontoxic and neither biologically nor otherwise undesirable, and which is acceptable for therapeutic or cosmetic use, in particular by topical application.

The dermatological and dermocosmetic compositions of the invention may be in the forms typically known for topical administration, i.e., in particular lotions, foams, gels, dispersions, emulsions, sprays, serums, masks or creams, with excipients enabling in particular cutaneous penetration so as to improve the active agent's properties and accessibility. Advantageously, it will be a cream.

These compositions generally contain, in addition to the compounds of the combination of the present invention, a physiologically acceptable medium, in general water- or solvent-based, for example alcohols, ethers or glycols. They can also contain surfactants, sequestering agents, preservatives, stabilizers, emulsifiers, thickeners, gelling agents, humectants, emollients, trace elements, essential oils, fragrances, colorants, mattifiers, chemical or mineral filters, moisturizers or spring water, etc.

Said compositions can further contain other active agents producing a complementary or possibly synergistic effect.

Advantageously, the compositions of the present invention will comprise 0.01% to 10% by weight, preferably 0.1% to 5% by weight, of the compound of formula (I) relative to the total weight of the composition.

Advantageously, the compositions of the present invention will comprise 0.001% to 5% by weight, preferably 0.01% to 1% by weight, of retinoid relative to the total weight of the composition.

These compositions are more particularly intended to prevent the formation of retentional lesions or to treat acne.

The present invention also concerns a retinoid for topical use in preventing the formation of retentional lesions.

The present invention also concerns the use of a retinoid for the manufacture of a dermatological or dermocosmetic topical composition for preventing the formation of retentional lesions.

The present invention also concerns a method for preventing the formation of retentional lesions comprising the topical administration of an effective amount of a retinoid to a person in need thereof.

Such a topical administration of a retinoid, for preventing the formation of retentional lesions, has the advantage of preventing sebaceous gland atrophy—notably encountered with oral administration of isotretinoin—and the advantage of being well tolerated (no side effects).

The retinoid used can be selected more particularly from retinol, retinaldehyde, and retinoic acid in its various isomeric forms (in particular all-trans, 13-cis and 9-cis). It can be in particular retinol or retinaldehyde. Preferably the retinoid is retinaldehyde.

The retinoid can in particular be combined with a compound of general formula (I) as defined above, and more particularly with the following Compound A:

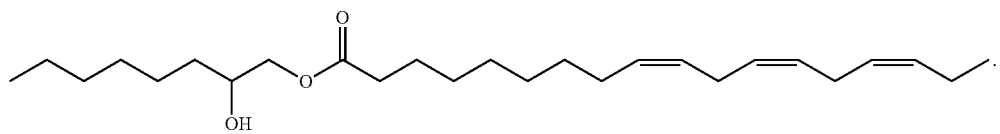

The present invention is illustrated by the following non-limiting examples.

FIGURE

The FIGURE shows the mean number of retentional lesions, as a function of time (T0, T3 weeks and T6 weeks), after topical treatment with cream comprising a retinaldehyde/Compound A combination.

EXAMPLES

I—Examples of Compositions Comprising a Retinoid or a Combination of the Invention COMPOSITION 1 (cream) containing retinaldehyde

| INCI name | Percentage by weight |
|---|---|
| Water | q.s. 100% |
| Glycerin | 6 |

-continued

| INCI name | Percentage by weight |
|---|---|
| Disodium EDTA | 0.1 |
| Phenoxyethanol | 0.35 |
| Glyceryl stearate & PEG-100 stearate | 2-5 |
| Dimethicone | 4 |
| Dicaprylyl carbonate | 3-6 |
| Butylhydroxytoluene | 0.02 |
| Retinaldehyde | 0.1 |
| PMMA | 2-7 |

COMPOSITION 2 (cream) containing a combination of the invention (retinaldehyde/Compound A)

| INCI name | Percentage by weight |
|---|---|
| Water | q.s. 100% |
| Glycerin | 6 |
| Disodium EDTA | 0.1 |
| Pentylene glycol | 3 |
| Glyceryl stearate & PEG-100 stearate | 3 |
| Isododecane | 7 |
| Butylhydroxytoluene | 0.02 |
| Carbomer papain crosspolymer | 1 |
| Retinaldehyde | 0.1 |
| Caprylic/Capric triglycerides | 7 |
| Compound A | 0.6 |

II—Clinical Studies

II-1. Clinical Study of Cream Comprising a Retinaldehyde/Compound A Combination

The clinical trial was an open study involving 60 subjects (men and women) between 12 and 35 years of age with mild to moderate acne for purposes of testing the tolerance and efficacy of Composition 2.

All of the participants initially had more than 10 retentional lesions (open and closed comedones) on their skin (excluding the nasal pyramid).

The cream was applied to the face (clean skin) in the evening by means of gentle massage.

The lesions were counted at T0 (before the first treatment), T3 weeks and T6 weeks according to the method described by Lucky (Lucky AW et al. (1996)). The results obtained concerning the number of retentional lesions are presented in the table below and in The FIGURE:

| | Number of retentional lesions | |
|---|---|---|
| Time | Mean | p-value |
| T0 | 26.8 | — |
| T3 weeks | 13.3 | <0.0001 |
| T6 weeks | 10.0 | <0.0001 |

A significant decrease in the number of retentional lesions is thus observed after 3 weeks of treatment with cream containing a retinaldehyde/Compound A combination of the invention (49%) and is 63% after 6 weeks.

II-2. Clinical Study of Cream Comprising Retinaldehyde without Compound A

The clinical trial was an open study involving 29 subjects (men and women) between 12 and 35 years of age with mild to moderate acne for purposes of testing the tolerance and efficacy of cream having the following composition:

| INCI name | Percentage by weight |
|---|---|
| Water | q.s. 100% |
| Potassium sorbate | 0.3 |
| Ethanol | 3 |
| Glycolic acid | 6 |
| Ceteareth 33 & Cetearyl alcohol | 3 |
| Polysorbate 60 | 6 |
| Cetyl alcohol | 11 |
| Butylhydroxytoluene | 0.01 |
| Cyclopentasiloxane | 10 |
| Sodium hydroxide | q.s. |
| Retinaldehyde | 0.1 |
| Undecyl rhamnoside | 0.2 |

All of the participants initially had more than 10 retentional lesions (open and closed comedones) on their skin.

The cream was applied to the face (clean skin) in the evening by means of gentle massage.

The lesions were counted at T0, T3 weeks and T6 weeks.

II-3. Clinical Study of Cream Comprising Compound A without Retinoid

The clinical trial was an open study involving 46 subjects (men and women) between 12 and 35 years of age with mild to moderate acne for purposes of testing the tolerance and efficacy of cream having the following composition:

| INCI name | Percentage by weight |
|---|---|
| Water | q.s. 100% |
| Glycerin | 6 |
| Disodium EDTA | 0.1 |
| Polyacrylate | 1 |
| Cetearyl glucoside & Cetearyl alcohol | 4 |
| Isohexadecane | 5 |
| Dimethicone | 3 |
| Glyceryl laurate | 0.6 |
| Carbomer papain crosspolymer | 1 |
| Compound A | 0.6 |

All of the participants initially had more than 10 retentional lesions (open and closed comedones) on their skin (excluding the nasal pyramid).

The cream was applied to the face (clean skin) twice per day (morning and evening) by means of gentle massage.

The lesions were counted at T0, T3 weeks and T6 weeks.

II-4. Conclusion

The results obtained with the three compositions comprising a retinaldehyde/Compound A combination, retinaldehyde alone or Compound A alone, respectively, in the clinical studies described above, are summarized in the table below:

| | Change in mean number of retentional lesions | |
|---|---|---|
| Composition comprising: | T = 3 weeks | T = 6 weeks |
| Retinaldehyde/Compound A combination | −49% | −63% |
| Retinaldehyde | −23% | −37% |
| Compound A | −6% | −19% |

These results show that retinaldehyde, alone or in combination with Compound A, has an effect on the decrease in the number of retentional lesions, showing a prophylactic effect on the formation of retentional lesions.

These results also show the synergistic activity of retinaldehyde in combination with Compound A. Indeed, after 3 weeks, this combination reduces the number of retentional lesions by about half (49%). On the contrary, the cumulative result of the action of retinaldehyde alone and Compound A alone reduces the number of retentional lesions by 29% after 3 weeks of treatment. This result is also confirmed at T6 weeks.

Such a decrease in the number of retentional lesions, observed in a clinical setting, confirms the fact that the combination of the invention acts not only on the healing of existing retentional lesions but above all by preventing the appearance of new retentional lesions.

Thus this result confirms that the combination of the invention creates a favorable environment in the pilosebaceous unit for preventing new acne-prone sebaceous glands of the face from entering the acne cycle, i.e., for very significantly decreasing the number of new sebaceous glands entering the acne cycle.

III—In Vitro Studies: Retinaldehyde Inhibition of Genes Responsible for Differentiation in Keratinocytes
Materials and Methods:

In these experiments, retinaldehyde was applied topically for 24 hours at a concentration of 0.025% dissolved in Myritol on human skin explants (of 3 donors) kept alive in culture medium (Dulbecco's Modified Eagle Medium (DMEM)+10% fetal bovine serum (FBS)).

Myritol alone was used as the control.

At the conclusion of this treatment, the RNA is extracted, inspected for quality, and analyzed by means of a microarray (Agilent Technology).

Results:

The modulation of the genes of interest in human skin is presented in the tables below. They are averaged fold-change values below 1.8 (p<0.05). A fold change of −2.00 corresponds to a decrease in gene expression of about 50%.

Genes associated with targets of terminal keratinocyte differentiation:

| Fold change | p | Symbol | Gene name |
|---|---|---|---|
| −1.77 | 0.056 | DSG3 | desmoglein 3 |
| −1.70 | 0.058 | DSC1 | desmocollin 1 |
| −1.68 | 0.070 | DSG1 | desmoglein 1 |
| −1.55 | 0.095 | DSC3 | desmocollin 3 |
| −1.49 | 0.052 | CDSN | corneodesmosin |
| −1.60 | 0.042 | EPPK1 | epiplakin 1 |
| −1.53 | 0.091 | UPK2 | uroplakin 2 |
| −1.41 | 0.072 | EVPL | envoplakin |
| −2.73 | 0.115 | LCE3A | late cornified envelope 3A |
| −1.90 | 0.271 | LCE3D | late cornified envelope 3D |
| −1.56 | 0.004 | CNFN | cornifelin |

Genes associated with keratins:

| Fold change | p | Symbol | Gene name |
|---|---|---|---|
| −4.68 | 0.115 | KRTAP11-1 | keratin associated protein 11-1 |
| −3.61 | 0.015 | KRT6C | keratin 6C |
| −2.83 | 0.012 | KRT6A | keratin 6A |
| −2.71 | 0.016 | FLJ46111 | keratin 8 pseudogene |
| −2.66 | 0.372 | KRT27 | keratin 27 |
| −2.63 | 0.027 | KRT16 | keratin 16 |
| −2.19 | 0.472 | KRT86 | keratin 86 |
| −2.09 | 0.288 | KRTAP3-1 | keratin associated protein 3-1 |
| −1.83 | 0.325 | KRT6B | keratin 6B |
| −1.81 | 0.009 | KRTCAP3 | keratinocyte associated protein 3 |

It was thus shown that retinaldehyde inhibits 13 targets of terminal keratinocyte differentiation and 11 keratins, leading to a decrease in the differentiation of skin epidermis. This contributes to the beneficial effect of retinaldehyde in improving the change in the keratinization process leading to comedogenesis.

Likewise, these results are strengthened by the absence of induction by retinaldehyde of keratinocyte proliferation, because the proliferation of ductal epithelium is a key factor involved in comedogenesis (Cunliffe W J et al. (2004)).

Conclusion:

These results show that retinaldehyde (RAL):
inhibits keratinocyte differentiation, and
does not increase cell proliferation.

The modulation of keratinocyte differentiation allows retinaldehyde to have a prophylactic action on the formation of retentional lesions by a protective effect on the epithelium of the infundibular canal. Furthermore, the fact that retinaldehyde does not act on cell proliferation also makes it possible to avoid thickening of the canal.

The whole of these data shows the role of retinaldehyde in protecting the infundibular canal by preventing thickening/keratinization of the canal.

Therefore, that shows that retinal can be used in the prevention of retentional lesions.

REFERENCES

WO 2010/072738

Cunliffe W J et al. *Comedone formation: etiology, clinical presentation, and treatment.* Clin. Dermatol. 2004, 22:367-374.

Everts H B *Endogenous retinoids in the hair follicle and sebaceous gland.* Biochim. Biophys. Acta 2012, 1821: 222-229.

Lucky A W et al. *A multirater validation study to assess the reliability of acne lesion counting.* J. Am. Acad. Dermatol. 1996 October; 35(4):559-65.

Shaheen B and Gonzalez M *Acne sans P. acnes.* J. Eur. Acad. Dermatol. Venereol. 2013, 27:1-10.

21. The method according to claim 18, wherein the compound of general formula (I) is:
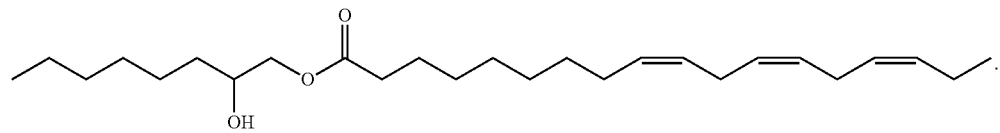

The invention claimed is:

1. A combination comprising a retinoid and a compound of the following general formula (I):

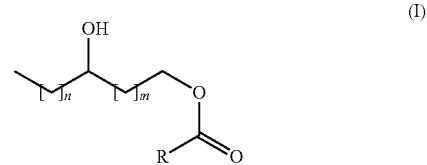

wherein:
n is an integer between 0 and 15,
m is 0, 1, 2 or 3, and
R is the hydrocarbon chain of a polyunsaturated fatty acid selected from omega-3s and omega-6s.

2. The combination according to claim 1, wherein n is between 1 and 10.

3. The combination according to claim 2, wherein n is 1, 2, 3, 4 or 5.

4. The combination according to claim 1, wherein m is 0 or 1.

5. The combination according to claim 1, wherein the polyunsaturated fatty acid is selected from α-linolenic acid, stearidonic acid, eicosatrienoic acid, eicosatetraenoic acid, eicosapentaenoic acid, docosapentaenoic acid, docosahexaenoic acid, tetracosapentaenoic acid, tetracosahexaenoic acid, linoleic acid, gamma-linolenic acid, eicosadienoic acid, dihomo-gamma-linolenic acid, arachidonic acid, docosatetraenoic acid, docosapentaenoic acid, adrenic acid and calendic acid.

6. The combination according to claim 5, wherein the polyunsaturated fatty acid is a α-linolenic acid, stearidonic acid or linoleic acid.

7. The combination according to claim 1, wherein the compound of general formula (I) is selected from the following molecules:

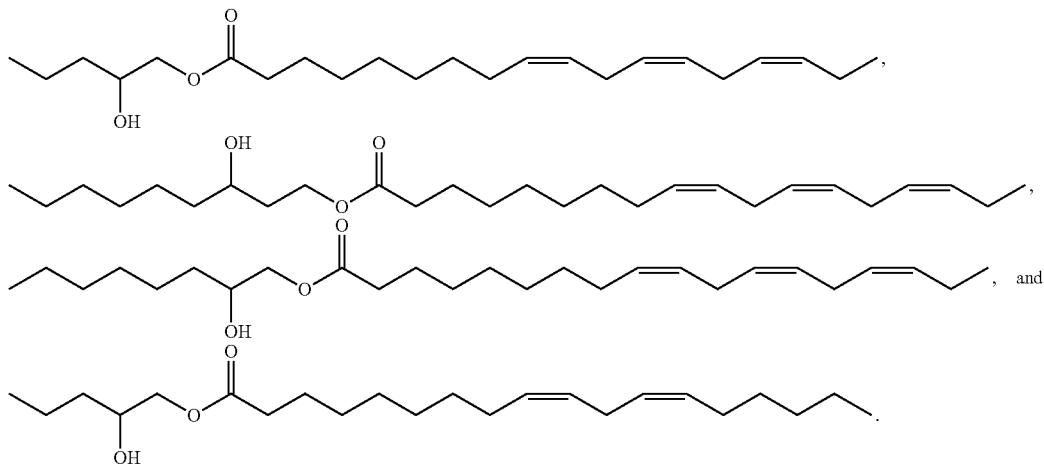

8. The combination according to claim 1, wherein the retinoid is selected from retinol, retinaldehyde, and retinoic acid in its various stereoisomeric forms.

9. The combination according to claim 1, wherein the retinoid is retinaldehyde and the compound of general formula (I) is:

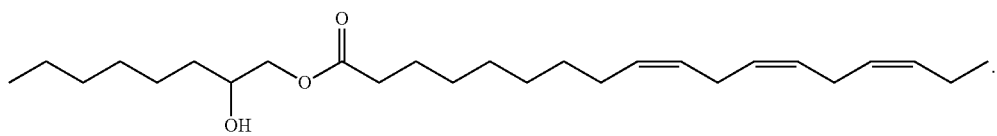

10. A method for preventing the formation of retentional lesions or for treating acne comprising the administration to a patient in need thereof of an effective amount of a combination according to claim 1.

11. A dermatological or dermocosmetic composition comprising at least one combination according to claim 1 in association with at least one dermatologically or dermocosmetically acceptable excipient.

12. The dermatological or dermocosmetic composition according to claim 11, wherein it comprises 0.01% to 10% by weight of the compound of formula (I) relative to the total weight of the composition.

13. The dermatological or dermocosmetic composition according to claim 12, wherein it comprises 0.1% to 5% by weight of the compound of formula (I) relative to the total weight of the composition.

14. The dermatological or dermocosmetic composition according to claim 11, wherein it comprises 0.001% to 5% by weight, of retinoid relative to the total weight of the composition.

15. The dermatological or dermocosmetic composition according to claim 14, wherein it comprises 0.01% to 1% by weight of retinoid relative to the total weight of the composition.

16. The dermatological or dermocosmetic composition according to claim 11, wherein it is for topical application.

17. A method for preventing the formation of retentional lesions or for treating acne comprising the administration to a patient in need thereof of an effective amount of a dermatological or dermocosmetic composition according to claim 11.

18. A method for preventing the formation of retentional lesions comprising the topical administration to a patient in need thereof of an effective amount of a combination of a retinoid and a compound of the following formula (I);

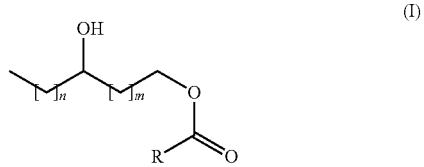

wherein:
n is an integer between 0 and 15,
m is 0, 1, 2 or 3, and
R is the hydrocarbon chain of a polyunsaturated fatty acid selected from omega-3s and omega-6s.

19. The method according to claim 18, wherein the retinoid is selected from retinol, retinaldehyde, and retinoic acid in its various stereoisomeric forms.

20. The method according to claim 19, wherein the retinoid is retinaldehyde.